United States Patent [19] [11] 4,384,137
Schouteeten et al. [45] May 17, 1983

[54] PROCESS FOR PREPARATION OF HYDROXYARYLGLYOXYLIC ACIDS AND THEIR ALKALINE SALTS, AND APPLICATION THEREOF TO PREPARATION OF SODIUM PARAHYDROXYPHENYLGLYOXYLATE

[75] Inventors: Alain Schouteeten, Ezanville; Yani Christidis; Jean-Claude Vallejos, both of Paris, all of France

[73] Assignee: Societe Francaise Hoechst, France

[21] Appl. No.: 375,124

[22] PCT Filed: Aug. 27, 1981

[86] PCT No.: PCT/FR81/00108
§ 371 Date: Apr. 20, 1982
§ 102(e) Date: Apr. 20, 1982

[87] PCT Pub. No.: WO82/00821
PCT Pub. Date: Mar. 18, 1982

[30] Foreign Application Priority Data

Sep. 4, 1980 [FR] France .................................. 80 19103

[51] Int. Cl.³ ........................ C07C 59/90; C07C 65/40
[52] U.S. Cl. .................................................... 562/463
[58] Field of Search ........................................ 562/463

[56] References Cited

U.S. PATENT DOCUMENTS 3,846,470 11/1974 Raabe et al. .
3,943,169 3/1976 Murcita et al. ..................... 562/463

OTHER PUBLICATIONS

L. Bouveault, Bull. Soc. Chim. France 1898 (3) 19, 75.
P. Francis et al., Annalen, 1911, 382, 206.
Guyot, A. et al., Bull. Soc. Chim. France, 1910 (4), 7, 902–913.

*Primary Examiner*—Paul J. Killos
*Attorney, Agent, or Firm*—Karl W. Flocks; Sheridan Neimark

[57] ABSTRACT

The invention relates to a process for preparation of hydroxyarylglyoxylic acids starting from hydroxyarylglycolic acids, by catalytic oxidation in an aqueous alkaline medium to pH higher than, or equal to, 11.5, through oxygen or oxygen-containing gas, characterized in that it is carried out in homogeneous phase at a temperature lower than, or equal to, 30° C., and in the presence of cupric ions, and in that at the end of the reaction, the desired acid is isolated from the reactional medium through acidification to pH of about 0.5.

The sodium parahydroxyphenylglyoxylate is obtained when acidification is stopped at pH=5, at the end of the reaction.

8 Claims, No Drawings

PROCESS FOR PREPARATION OF HYDROXYARYLGLYOXYLIC ACIDS AND THEIR ALKALINE SALTS, AND APPLICATION THEREOF TO PREPARATION OF SODIUM PARAHYDROXYPHENYLGLYOXYLATE

This invention relates to a novel process for preparation of hydroxyarylglyoxylic acids and their alkaline salts, and application thereof to the preparation of sodium parahydroxyphenylglyoxylate crystallized anhydrous or with two molecules of water.

Hydroxyarylglyoxylic acids are precious raw materials to have access among others to hydroxylated aromatic aldehydes by decarboxylating degradation. The easy decarboxylation of arylglyoxylic acids and fragility of arylglycolic acids to the oxidation supplying by decarboxylating degradation the corresponding aromatic aldehyde, has for a long time rendered the preparation of arylglyoxylic acids redhibitory by oxidation of the corresponding arylglycolic acids. For the preparation of such acids, for the last few years, indirect methods have been employed, either by condensation of ethoxalyl chloride on an alkoxy benzene followed by alkaline hydrolysis of the ester and ether functions, according to L. BOUVEAULT, Bull.Soc.chim. France, 1898, (3), 19, 75, or by hydrolysis in an aqueous medium of an oxaloaryldiazonium sulfate obtained by diazotation in a sulfuric medium of an aminoarylglyoxylic acid generally resulting from permanganic oxidation in an aqueous alkaline medium of an aminoacetophenone previously acylated with nitrogen, according to J. Aloy and Ch. Rabaut, Bull.Soc.chim. France, 1911, (4), 9, 763, or by permanganic oxidation in an alkaline medium of a hydroxyacetophenone, according to the Italian patent 475 964 or by alkaline hydrolysis of a benzoylcyanide, according to P. Francis et al., Annalen, 1911 382, 206, or by chromic oxidation of a mandelamide according to M. S. Mashevskaya, Khim,Prom., 1979, 2; 5–7 (C.A. 1979, 91,211037j), or finally, by Hoesch's reaction (K. Hoesch, Ber., 1915, 48, 1122).

Such preparation processes, however, either use toxic, dangerous or expensive reactives or supply the desired acids with a low yield, or finally, require the use of rare raw materials.

Recently, a process for oxidation of arylglycolic acids into arylglyoxylic acids has been described in the European patent application No. 0 005 779. According to such process, the oxidation is effected through oxygen in an aqueous alkaline medium, in the presence of a catalyst deposited on carbon black and constituted by platinum or palladium activated by a lead or bismuth salt.

But this preparation process requires expensive catalysts which, due to unavoidable losses upon the recovery and recycling operations, result in high manufacturing costs.

The Applicant has now discovered a novel economical process for preparation of hydroxyarylglyoxylic acids from hydroxyarylglycolic acids, which eliminates such disadvantages.

This process which is the object of the present invention is a process for catalytic oxidation through oxygen in an aqueous alkaline medium, characterized in that it is carried out at the ambient temperature and in homogeneous catalysis with cupric ions.

Cupric ions are known as capable of oxidizing certain carbonylated structures such as e.g. acyloins. Until now, however, to the Applicant's knowledge, when they had been used for oxidizing alpha-hydroxylated carboxylic acids, they were causing an oxidizing scission into carbonylated derivatives having one carbon atom less than the starting acid and into carbon dioxide.

Thus, on studying novel syntheses of vanillin, A. Guyot and A. Gry, Bull.Soc.chim. France, 1910, (4), 7, 902–913, were not capable to oxidize 4-hydroxy-3-methoxy-phenylglycolic acid into 4-hydroxy-3-methoxy-phenylglyoxylic acid, in spite of the use of varied conditions and more particularly utilization of cupric sulfate; they obtained only vanillin or products derived therefrom by resinification.

The process which is the object of this invention is carried out at the ambient temperature or at a temperature close to the ambient temperature. Since oxidation of a secondary alcohol into carbonyl is exothermic, it is therefore often necessary to cool the reactional medium during oxidation. As a matter of fact, the Applicant has noted that an increase in the temperature was damaging to the selectivity of the oxidation, and was preferentially orienting it toward a decarboxylating oxidizing degradation into aldehydic derivatives.

The process which is the object of this invention is carried out in an aqueous alkaline medium at a pH higher than, or equal to 11.5. According to an advantageous mode, it is implemented starting from an aqueous solution of a concentration comprised between 0.3 M and 2 M of hydroxyarylglycolic acid and in the presence of an excess of alkaline metal hydroxide, such as sodium hydroxide, with respect to the required stoichiometry for salifying the carboxylic function and the phenolic function(s) present on the starting acid. Advantageously, such excess is higher than or equal to 0.5 mole of sodium hydroxide per mole of hydroxyarylglycolic acid used.

The process which is the object of the invention is carried out in an aqueous alkaline medium at a pH higher than, or equal to, 11.5 and in the presence of cupric ions, $Cu^{++}$ in catalytic quantity. Advantageously, from 0.1 to 0.01 atom/gram of copper is used in form of cupric ions, and preferentially, from 0.05 to 0.08 atom/gram of copper in form of cupric ions per mole of hydroxyarylglycolic acid used. The cupric ions are advantageously brought to the reactional medium by addition of a mineral or organic salt of copper II such as e.g. the anhydrous or hydrated cupric sulfate, the cupric acetate.

The process which is the object of this invention is carried out in the presence of oxygen or an oxygen-containing gas. In view of the low solubility of oxygen in water, at the ambient pressure and temperature, the process is generally implemented under an oxygen pressure lower than, or equal to, 10 bars, and advantageously, an oxygen pressure of 8 bars. When the process is realized under a lower oxygen pressure, such as e.g. a pressure of 2 bars, instead of 8 bars, there can be noted a slower reactional speed requiring a slightly longer reactional duration to obtain the same yield, but the selectivity of the process is not modified thereby.

At the end of the reaction, after filtration to eliminate some mechanical impurities, followed if necessary by a separation at pH=5 of the possibly formed aldehydic derivative, the obtained hydroxyarylglyoxylic acid is extracted from the reactional medium previously acidified to pH=0.5 with a strong mineral acid such as concentrated hydrochloric acid, with a solvent little or not miscible in water such as ethyl acetate. After elimination under vacuum of the extraction solvent, the desired hydroxyarylglyoxylic acid is isolated, generally, in crystallized form, sufficiently pure to be used as such, otherwise a simple hot and cold recrystallization in a suitable solvent permits purification thereof. Once the acid has been thus obtained, it is easy to obtain the corresponding salts, by neutralization reaction by using means known in themselves.

Another object of this invention is the application of such process to the more particular preparation of the sodium parahydroxyphenylglyoxylate crystallized pure anhydrous or solvated with two molecules of water.

To the Applicant's knowledge, such anhydrous or hydrated salt has not been described in the Literature, and due to its noted low solubility in cold water, it may constitute convenient means for isolating and/or purifying parahydroxyphenylglyoxylic acid.

As a matter of fact, to obtain sodium parahydroxyphenylglyoxylate crystallized pure with two molecules of solvation water it is sufficient, at the end of the oxidation reaction of parahydroxyphenylglycolic acid and after filtration, to stop acidification of the reactional medium at pH=5, with concentrated hydrochloric acid, then filtrate the obtained precipitate, and thereafter, to dry it under vacuum, at constant weight, at a temperature lower than, or equal to, 60° C. The sodium parahydroxyphenylglyoxylate crystallized pure anhydrous is obtained by drying at 75° C. under vacuum at constant weight the sodium parahydroxyphenylglyoxylate crystallized pure with two molecules of solvation water. The corresponding acid can then be obtained by displacement of such salt by a strong mineral acid according to means known in themselves.

The following examples will permit to better understand the invention.

They are merely given in an illustrative manner but do not represent limitations of the invention.

EXAMPLE 1

There is agitated under an initial oxygen pressure of 8 bars and external cooling so as to maintain the internal temperature between 20° and 30° C., a solution obtained by dissolving in 546 g of water:

141.2 g (3.53 moles) of sodium hydroxide in pellets,
186.16 g (1 mole) of monohydrated p-hydroxymandelic acid,
11.2 g (0.07 mole) of anhydrous cupric sulfate.

The development of the reaction may be followed by liquid phase chromatography. To this end, a test sample is periodically taken from the reactional medium to determine parahydroxymandelic (PHM), parahydroxyphenylglyoxylic (PHPG), parahydroxybenzoic (PHB) and parahydroxybenzaldehyde (PHBZ) acids. These determinations are carried out by liquid chromatography with a PHILIPS apparatus at 25° C. under a pressure of 100 bars with a flow rate of 1 cm³ per mn of an acidified water-methanol 80-20 eluting mixture, and with a 240 nm-UV detection. The results obtained expressed in moles (±0.05 mole) in terms of time expressed in minutes are assembled in TABLE 1.

TABLE I

| Time | PHM | PHPG | PHB | PHBZ | TOTAL |
|---|---|---|---|---|---|
| 0 | 1 | 0 | 0 | 0 | 1 |
| 30 | 0.89 | 0.06 | 0 | 0 | 0.95 |
| 60 | 0.88 | 0.11 | 0 | 0 | 0.99 |
| 90 | 0.79 | 0.18 | 0 | 0.02 | 0.99 |
| 120 | 0.72 | 0.28 | 0 | 0.02 | 1.02 |
| 240 | 0.35 | 0.69 | 0 | 0.02 | 1.06 |

TABLE I-continued

| Time | PHM | PHPG | PHB | PHBZ | TOTAL |
|---|---|---|---|---|---|
| 300 | 0.26 | 0.75 | 0 | 0.05 | 1.06 |
| 1320 | 0.02 | 1 | 0 | 0.05 | 1.07 |

After agitation for 22 hours at 25°–30° C., with an oxygen pressure of 8 bars, the reactional medium brought to the ambient temperature is filtered to eliminate mechanical impurities, then the filtrate maintained at the ambient temperature is acidified to pH=5 with concentrated hydrochloric acid. The sodium salt of the p-hydroxyphenylglyoxylic acid crystallizes, it is dried out, then washed by impasting with 100 cm³ of ethyl acetate, then dried under vacuum at 60° C. at constant weight. Thus, there is collected 202.15 g (0.9 mole) of product crystallized with two molecules of water, i.e. a yield of 90% of the theoretical value, calculated with respect to the starting acid.

This salt can be recrystallized under hot and cold conditions in 4.5 volumes of water with a yield of 88%. Dried at 60° C. under vacuum, it keeps its crystallization water, but dried at 75° C., under vacuum for two hours, it leads to the anhydrous product. It presents at 20° C. a water-solubility of 2.5 g for 100 g.

Microanalysis

On the product dried at 60° C. at constant weight:

| $C_8H_5O_4$ Na,$2H_2O$ | C (%) | H (%) | $H_2O$ (%)+ |
|---|---|---|---|
| Calculated | 42.86 | 4.05 | 16.07 |
| Found | 43.0 | 4.2 | 16.3 |

+Determined according to K. Fischer's method.

On product dried at 75° C. at constant weight.

| $C_8H_5O_4$ Na | C (%) | H (%) | $H_2O$ (%) |
|---|---|---|---|
| Calculated | 51.07 | 2.68 | 0 |
| Found | 51.2 | 2.7 | 0 |

To the Applicant's knowledge, this product has never been described in the Literature.

This sodium salt brought into suspension in water acidified to pH=0.5 by concentrated hydrochloric acid quantitatively leads to p-hydroxyphenylglyoxylic acid. M.p.=177°–178° C. (R. D. Sprenger et al.; J.Amer.-Chem.Soc., 1950, 72, 2874, M.p. 177.5°–178° C.).

EXAMPLES 2–9

The Table II illustrates the examples 2 to 9. In this table the reactives are expressed in moles, the oxygen pressures in bars, the temperatures in °C., the reaction durations in hours, and the concentrations in grams of parahydroxymandelic acid for 100 g of the reactional solution. The yields of parahydroxyphenylglyoxylic acid have been determined by liquid chromatography over the raw reactional media; they are expressed in percentages of theoretical values as calculated with respect to the implemented parahydroxymandelic acid.

The selectivity expressed in percentage is the molar ratio of the parahydroxyphenylglyoxylic acid to the sum of parahydroxybenzoic acid, parahydroxyphenylglyoxylic acid and parahydroxybenzaldehyde formed during the reaction. The selectivity is given to ±1%.

The operative step mode used is similar to that described in Example 1.

TABLE II

| reactives conditions-results | N° of Example | | | | | | | |
|---|---|---|---|---|---|---|---|---|
| | 2 | 3 | 4 | 5 | 6 | 7 | 8 | 9 |
| PHM | 1 | 1 | 1 | 1 | 1 | 1 | 1 | 1 |
| Sodium hydroxide | 5.53 | 5.53 | 5.53 | 5.53 | 2 | 2.53 | 2.53 | 2.53 |
| Anhydrous cupric sulfate | 0.072 | 0.072 | 0.071 | 0 | 0.071 | 0.071 | 0.071 | 0.071 |
| Water | 51.2 | 51.2 | 26.85 | 23.4 | 36.6 | 18.93 | 33.53 | 33.53 |
| Total weights | 1322.3 | 1322.3 | 883.9 | 821.9 | 918.3 | 621.5 | 884.6 | 884.6 |
| Concentrations | 12.7 | 12.7 | 19 | 20.45 | 18.3 | 27.0 | 19 | 19 |
| Pressures | 8 | 8 | 8 | 8 | 8 | 8 | 2 | 8 |
| Temperatures | 50 | 25→43 | 27 ± 2 | 27 ± 2 | 27 ± 2 | 20 ± 2 | 19→30 | 23→31 |
| Durations | 11 | 22 | 20 | 22 | 21 | 22 | 21 | 7 |
| Yields | 86 | 90 | 92.8 | 11 | 22 | 94.5 | 74 | 85.6 |
| Selectivities | 90 | 95 | 99.8 | | | 96.7 | 96.5 | 96.7 |

EXAMPLE 10

There is agitated for 30 hours under an initial pressure of oxygen of 8 bars and under external cooling such as to maintain the temperature of the reactional medium between 20° and 30° C., a solution obtained by dissolving in 258 g (14.3 moles) of water:

90.6 g (2.26 moles) of sodium hydroxide in pellets;
101.25 g (0.5 mole) of 3-chloro-4-hydroxymandelic acid;
9 g (0.036 mole) of pentahydrated cupric sulfate.

At the end of the reaction, the reactional medium brought to the ambient pressure is filtered, then the filtrate maintained at the ambient temperature is acidified at pH=0.5 with concentrated hydrochloric acid, and it is thereafter submitted to successive extractions with ethyl acetate. Thus there is isolated after elimination of the extractions solvent, 87.4 g (0.436 mole) of 3-chloro-4-hydroxy-phenylglyoxylic acid having a melting point of 116°-117° C. (M.p.=114°-116° C., FUSISAWA Pharmaceutical Comp.Ltd. FR 2 299 869), i.e. a yield of 87.2% of the theoretical value.

EXAMPLE 11

It is proceeded according to Example 10, starting with a solution of:

90.6 g (2.26 mole) of sodium hydroxide in pellets;
123.1 g (0.5 mole) of monohydrated 3,5-dimethoxy-4-hydroxymandelic acid;
9.0 g (0.036 mole) of pentahydrated cupric sulfate;
308 g (17.1 moles) of water.

At the end of the reaction, the reactional medium brought to the ambient temperature is filtered, then the filtrate maintained at the ambient temperature is acidified at pH=5, with concentrated hydrochloric acid, and is then submitted to successive extractions with ethyl acetate. There is thus isolated after elimination under vacuum of the extraction solvent, 40.7 g (0.223 mole) of 3,5-dimethoxy-4-hydroxy-benzaldehyde; melting point=113° C. (M.p.=113° C., Beil. 8, 391). The extraction mother waters being united, are then acidified to pH=0.5, with concentrated hydrochloric acid, and then are submitted to repeated extractions with ethyl acetate.

Thus, there is isolated, after elimination under vacuum of the extraction solvent, 21.9 g (0.096 mole) of 3,5-methoxy-4-hydroxy-phenylglyoxylic acid having a melting point of 134±1° C. (M.p.=128° C., MAUTHNER, Annalen, 1913, 395, 276) i.e. a yield of 19.2% of the theoretical value.

EXAMPLE 12

It is proceeded as according to Example 11, starting from a solution of:

99 g (0.5 mole) of 4-hydroxy-3-methoxy-mandelic acid;
90.6 g (2.26 mole) of sodium hydroxide in pellets;
9 g (0.036 mole) of pentahydrated cupric sulfate;
258 g (14.3 moles) of water.

After treatments there is isolated 30.7 g (0.2 mole) of 4-hydroxy-3-methoxy-benzaldehyde. M.p.=81°-83° C. Beil., 8, 247) and 41.7 g (0.213 mole) of 4-hydroxy-3-methoxy-phenylglyoxylic acid, Melting point=133°-134° C. (M.p.=133°-134° C., Beil. 10, 988) i.e. a yield of 42.6% of the theoretical value.

It will be understood that this invention was only described in a merely explanatory and not limitative manner, and that any useful modification can be brought thereto without departing from its scope as defined in the claims following hereinafter.

We claim:

1. In a process for preparation of hydroxyarylglyoxylic acids, starting from hydroxyarylglycolic acids by catalytic oxidation in an aqueous alkaline medium, to a pH higher than, or equal to, 11.5 by oxygen or an oxygen-containing gas, the improvement in which said process is carried out in a homogeneous phase, at a temperature lower than, or equal to, 30° C., and in the presence of cupric ions, and at the end of the reaction, the desired acid is isolated by acidification from the reactional medium.

2. The improvement according to claim 1, in which there is used from 0.1 to 0.01 atom gram of copper in form of cupric ions per mole of hydroxyarylglycolic acid used.

3. The improvement according to claim 1, in which the cupric ions are brought to the reactional medium by a salt selected from the mineral and organic salts of copper II.

4. The improvement according to claim 3, in which said mineral and organic salts are selected from the anhydrous and hydrated cupric sulfates, and from the cupric acetate.

5. The improvement according to claim 1, according to which said process is carried out starting from an aqueous solution of a concentration comprised between 0.3 and 2 M of hydroxyarylglycolic acid, and in the presence of an excess of an alkaline hydroxide with respect to the required stoichiometry for salifying the carboxylic function and the phenolic function(s) present on the starting acid.

6. The improvement according to claim 1, according to which said process is applied to the preparation of sodium parahydroxyphenylglyoxylate, then of the corresponding acid, starting from parahydroxymandelic acid, and by acidifying at the end of the reaction, the reactional medium to pH=5 to isolate said sodium parahydroxyphenylglyoxylate, then by acidifying said isolated salt to pH=0.5 to isolate said corresponding acid.

7. The improvement according to claim 6, according to which said isolated sodium salt is dried under vacuum at constant weight at 60° C. to supply the corresponding salt crystallized with two molecules of water.

8. The improvement according to claim 6, according to which said isolated sodium salt is dried under vacuum at constant weight at 75° C. to supply the corresponding anhydrous salt.

* * * * *